US006468969B1

(12) United States Patent
Rana et al.

(10) Patent No.: US 6,468,969 B1
(45) Date of Patent: Oct. 22, 2002

(54) INHIBITION OF HIV-1 REPLICATION USING D-AMINO ACID PEPTIDES

(76) Inventors: Tariq M. Rana, 22 Johanna Ct., Piscataway, NJ (US) 08854; Ikramul Huq, 10 Redcliffe Ave. #2A, Highland Park, NJ (US) 08904

( * ) Notice: Subject to any disclaimer, the term of this patent is extended or adjusted under 35 U.S.C. 154(b) by 0 days.

(21) Appl. No.: 09/409,624

(22) Filed: Oct. 1, 1999

Related U.S. Application Data

(63) Continuation of application No. 08/914,104, filed on Aug. 19, 1997, now abandoned.

(51) Int. Cl.[7] ........................ A61K 38/00; A61K 38/16; C07K 14/00; C07K 5/00
(52) U.S. Cl. ............................ 514/12; 514/12; 514/14; 514/15; 514/16; 514/18; 530/324; 530/327; 530/328; 530/329; 530/334; 530/331; 530/344; 435/235.1
(58) Field of Search .............................. 514/16, 12, 14, 514/18, 15; 530/324, 334, 331, 344, 328, 327, 329; 435/235.1

(56) References Cited

U.S. PATENT DOCUMENTS

| 5,079,231 A | | 1/1992 | Brunetti et al. | |
| 5,225,400 A | | 7/1993 | Brunetti et al. | |
| 5,492,896 A | | 2/1996 | Häbich et al. | |
| 5,646,120 A | * | 7/1997 | Sumner-Smith | ............. 514/14 |
| 5,767,083 A | | 6/1998 | Abajian et al. | |

FOREIGN PATENT DOCUMENTS

| WO | WO 86/04334 | | 7/1986 | |
| WO | WO-8912461 A1 | * | 12/1989 | .......... A61K/39/12 |
| WO | WO 96/22760 | | 8/1996 | |
| WO | WO97/12907 | | 4/1997 | |
| WO | WO98/47913 | | 10/1998 | |

OTHER PUBLICATIONS

Huq, et al. Nature Structural Biology 4:881–882 (1997).

* cited by examiner

Primary Examiner—Karen Cochrane Carlson
Assistant Examiner—Chih-Min Kam
(74) Attorney, Agent, or Firm—Lyon & Lyon LLP

(57) ABSTRACT

The Tat-inhibitory polypeptide derivatives of the formula I D-Cys-D-Phe-D-Thr-D-Thr-D-Lys-D-Ala-D-Leu-D-Gly-D-Ile-D-Ser-D-Tyr-D-Gly-D-Arg-D-Lys-D-Lys-D-Arg-D-Arg-D-Gln-D-Arg-D-Arg-D-Arg-D-Pro-D-Pro-D-Gln-D-Gly-D-Ser-D-Gln-D-Thr-D-His-D-Gln-D-Val-D-Ser-D-Leu-D-Ser-D-Lys-D-Gln (SEQ ID 1) and fragments or analogs thereof, and the biologically and pharmaceutically acceptable salts thereof exhibit advantageous properties, including binding to ΔTAR, inhibition of LTR-dependent reporter gene expression in a model cell assay and, finally, inhibition of HIV-1 replication, as determined in assays of HIV-induced syncytium formation, cytotoxicity and reverse transcriptase production. These peptides are thus capable of competing with the TAR RNA-binding domain of Tat protein and thus are useful as a therapeutic agents in the treatment of AIDS.

5 Claims, 7 Drawing Sheets

SEQUENCE LISTING

```
<160> NUMBER OF SEQ ID NOS: 5

<210> SEQ ID NO 1
<211> LENGTH: 36
<212> TYPE: PRT
<213> ORGANISM: Artificial Sequence
<220> FEATURE:
<223> OTHER INFORMATION: Description of Artificial Sequence:
      D-enantiomer of a tat-derived peptide.
<220> FEATURE:
<223> OTHER INFORMATION: All amino acids in this sequence are D amino
      acids.

<400> SEQUENCE: 1

Cys Phe Thr Thr Lys Ala Leu Gly Ile Ser Tyr Gly Arg Lys Lys Arg
 1               5                  10                  15

Arg Gln Arg Arg Arg Pro Pro Gln Gly Ser Gln Thr His Gln Val Ser
             20                  25                  30

Leu Ser Lys Gln
         35

<210> SEQ ID NO 2
<211> LENGTH: 36
<212> TYPE: PRT
<213> ORGANISM: Human immunodeficiency virus type 1

<400> SEQUENCE: 2

Cys Phe Thr Thr Lys Ala Leu Gly Ile Ser Tyr Gly Arg Lys Lys Arg
 1               5                  10                  15

Arg Gln Arg Arg Arg Pro Pro Gln Gly Ser Gln Thr His Gln Val Ser
             20                  25                  30

Leu Ser Lys Gln
         35

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: All amino
      acids are D amino acids and carboxy terminal is
      modified to N-acetyl-D-Arg

<400> SEQUENCE: 3

Arg Arg Arg Arg Arg Arg Arg Arg Arg
 1               5

<210> SEQ ID NO 4
<211> LENGTH: 23
<212> TYPE: RNA
```

```
<213> ORGANISM: Human immunodeficiency virus type 1

<400> SEQUENCE: 4
ggcagaucug agccugggag cuc                                          23

<210> SEQ ID NO 5
<211> LENGTH: 20
<212> TYPE: RNA
<213> ORGANISM: Human immunodeficiency virus type 1

<400> SEQUENCE: 5
ggcgccagau ccgagccacc                                              20
```

INHIBITION OF HIV-1 REPLICATION USING D-AMINO ACID PEPTIDES

This application is a Continuation of application Ser. No. 08/914,104, filed Aug. 19, 1997, now abandoned.

The research leading to the present invention was supported, at least in part, by a grant from the National Institutes of Health Grant No. AI41404. Accordingly, the U.S. Government may have certain rights in the invention.

BACKGROUND OF THE INVENTION

RNA-protein interactions are important in many cellular functions, including transcription. RNA splicing, and translation. One example of such an interaction is the mechanism of trans-activation of the human immunodeficiency virus type 1 (HIV-1) gene expression that requires the interaction of Tat protein with the trans-activation responsive region (TAR) RNA, a 59-base stem-loop structure located at the 5'-end of all nascent HIV-1 transcripts[1].

The promoter of HIV-1, located in the U3 region of the viral long terminal repeat (LTR), is an inducible promoter which can be stimulated by the trans-activator protein, Tat[1]. As in other lentiviruses, Tat protein is essential for trans-activation of viral gene expression[2-6].

Tat-derived peptides containing the arginine-rich RNA-binding domain of Tat are able to form in vitro complexes with TAR RNA[7-14]. Structural studies of Tat protein show that the RNA-binding domain is not a rigid helix[15]. Since the RNA-binding domain of Tat has a flexible structure, the symmetry of small peptides containing arginine-rich sequences may not be crucial in TAR RNA recognition. Recent syntheses of two D-enantiomeric proteins demonstrated that these proteins have optical properties, substrate specificity[16], and a structure[17,13] that mirrors those of the naturally occurring L-proteins. A powerful method to identify D-peptide ligands through mirror-image phage display has been recently discovered and a cyclic D-peptide was identified that interacts with the Src homology 3 domain of c-Src[19]. Due to the difference in chirality, D-peptides are resistant to proteolytic degradation and cannot be efficiently processed for major histocompatibility complex class II-restricted presentation to T helper cells ($T_H$ cells). Consequently, D-peptides would not induce a vigorous humoral immune response that impairs the activity of L-peptide drugs[20].

SUMMARY OF THE INVENTION

The present invention concerns Tat-inhibitory polypeptide derivatives. More particularly, this invention relates to polypeptides of the formula I D-Cys-D-Phe-D-Thr-D-Thr-D-Lys-D-Ala-D-Leu-D-Gly-D-Ile-D-Ser-D-Tyr-D-Gly-D-Arg-D-Lys-D-Lys-D-Arg-D-Arg-D-Gln-D-Arg-D-Arg-D-Arg-D-Pro-D-Pro-D-Gln-D-Gly-D-Ser-D-Gln-D-Thr-D-His-D-Gln-D-Val-D-Ser-D-Leu-D-Ser-D-Lys-D-Gln (SEQ ID 1)

and fragments and analogs thereof, and the biologically and pharmaceutically acceptable salts thereof, which exhibit advantageous properties, including binding to ΔTAR, inhibition of LTR-dependent reporter gene expression in a model cell assay and, finally, inhibition of HIV-1 replication, as determined in assays of HIV-induced syncytium formation, cytotoxicity and reverse transcriptase production. These compounds are thus useful in the treatment of HIV-1 infection by virtue of their ability to block the interaction of Tat protein with TAR RNA, thereby interfering with the transactivation step in the replication cycle of HIV-1. The rationale for this approach is that such peptides compete with the full length Tat protein for binding to TAR RNA, thereby preventing the required interactions between other domains in Tat protein and the nascent transcription apparatus.

It is an object of the present invention to provide compounds which are useful in the treatment of HIV-1 by virtue of their ability to block the interaction of Tat protein with TAR RNA, thereby interfering with the trans activation step in the replication cycle of this virus.

It is further an object of this invention to provide pharmaceutical compositions suitable for the administration of such compounds.

It is a still further object of the present invention to provide a method of treating HIV-1 infection in mammals which comprises the administration of the compounds of the present invention.

BRIEF DESCRIPTION OF THE DRAWING FIGURES

FIG. 1A is the sequence for the 36-residue peptide, amino acids 37 to 72, containing the RNA-binding domain of Tat (SEQ ID NO:2). The arginine rich region of Tat, corresponding to the Tat 48–57 peptide, is boxed.

FIG. 1B is a sequence showing the secondary structure of wild-type TAR RNA. Wild-type TAR RNA spans the minimal sequences that are required for Tat responsiveness in vivo[31] and for in vitro binding of Tat-derived peptides[7]. Wild-type TAR contains two non-wild-type base pairs to increase transcription by T7 RNA polymerase[25]. Mutant TAR RNAs (M0, M1, and M2) contained different numbers of mismatch bases in the pyrimidine bulge: M0, without bulge bases; M1, one Uridine bulge base; M2, two Uridines bulge. In mutant G26C, a base-pair in the upper stem of TAR RNA, G26–C39 was substituted by C26–G39.

FIG. 1C is the sequence showing the secondary structure of the designed duplex TAR RNA used in photocrosslinking experiments[24]. Duplex RNA contains the nucleotides C18 to C29 and G36 to G44 from the wild-type TAR RNA sequence, and extra flanking base pairs to enhance hybridization of the two RNA strands. Numbering of nucleotides in the duplex TAR RNA corresponds to their positions in wild-type TAR RNA.

FIG. 2 is a photograph showing the electrophoretic mobility shift analysis for the D-Tat peptide binding to wild-type (wild) and mutant M0 (mut) TAR RNA. The final concentration of RNA and peptides were 0.1 and 0.5 μM, respectively. RNA-peptide complexes are indicated as R-P.

FIG. 3 is a photograph showing the specificity of the D-Tat-TAR complex formation determined by competition assays. RNA-peptide complexes were formed between $^{32}P$-5'-end labeled TAR RNA (0.1 μM) and the D-Tat peptide (0.25 μM) in the presence of increasing concentrations of unlabeled wild-type or mutant TAR RNAs. Concentrations of the competitor RNAs in lanes 1, 2, 3, 4, 5, 6 were 0, 0.2, 0.4. 0.6. 0.8, and 1.2 μM, respectively. Lane M is a marker lane and RNA-peptide complexes are labeled as RP.

FIG. 4 is a photograph showing the site-specific photocrosslinking reaction of TAR RNA duplex labeled with 4-thioUracil at position 23 with the D-Tat peptide[24]. The RNA-RNA and RNA-peptide crosslink are indicated by R-R and R-P XL, respectively.

FIG. 5 is a photograph showing the inhibition of Tat-TAR complex formation by D-Tat peptide. Photocrosslinking of 4-thioU containing duplex TAR RNA was performed with L-Tat peptide (lane 2) and the RNA-protein crosslink digested with proteinase K (lane 3). Increasing amounts of D-Tat were added during RNA-protein complex formation, followed by photocrosslinking and protease digestion (lanes 4–9). Lane 1 is a control lane without any peptide. The RNA-RNA, RNA-peptide crosslink, and protease digest products containing small peptides are indicated by R-R XL, R-P XL, and R-P-XL, respectively.

Figure 6:
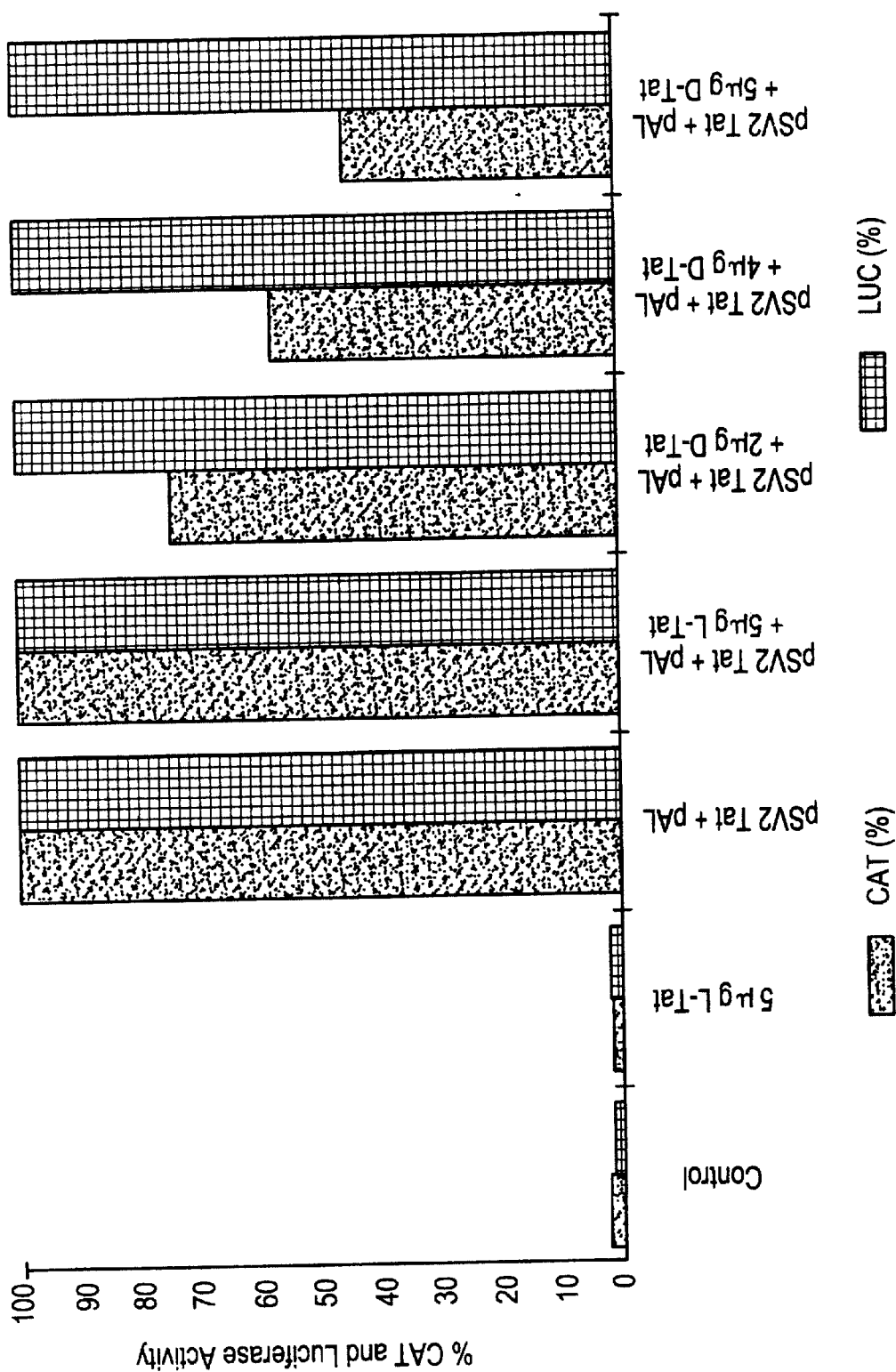

FIG. 6 is a graph showing the inhibition of Tat transactivation by the D-Tat (37–72) peptide (SEQ ID NO:1). CAT activity expressed from the integrated HIV-1 LTR of HL3T1 cells with several concentrations of D-Tat peptide is shown. Luciferase activity was a control experiment to determine the transfection inhibition of pSV2Tat by the addition of D-Tat. Transfection and enzymatic activity (CAT and Luciferase) assays were performed as described previously[26,27]. CAT and Luciferase activities were measured from multiple experiments and normalized to 100%. Control lane does not contain pSV2Tat or pAL and shows basal level of transcription.

Figure 7:
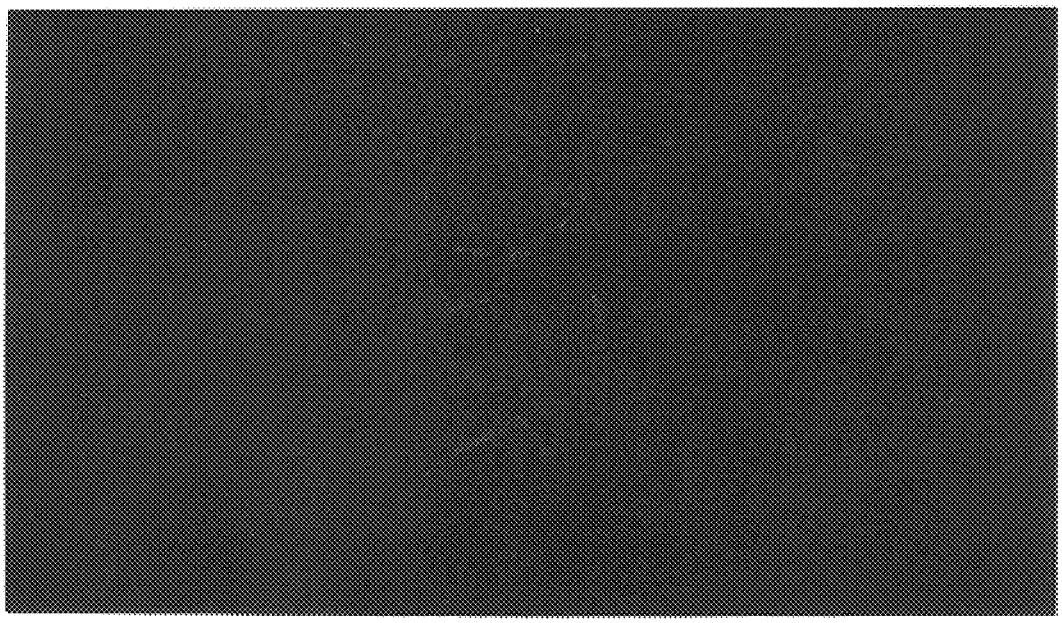

FIG. 7 is a model for the structure of TAR RNA and ribbon representation of two mirror-image Tat(37–72) peptides. For clarity, only the Tat(37–72) ribbon structure is shown. (Right) L-Tat based on NMR coordinates and (Left) mirror-image of L-Tat. TAR RNA, in the middle, shows widened major groove in the trinucleotide bulge region. Ribbon structure of TAR RNA is illustrated in five yellow lines and nucleotides in red. Tat peptide backbone is illustrated in five cyan lines, arginine sidechains in green, and arninoterminal cysteine in white. The structures of TAR RNA[32] and Tat protein[15] are based on NMR data. The structures of RNA and protein were visualized using Insight II software on an IRIS work station.

DETAILED DESCRIPTION OF THE INVENTION

The Tat protein of human immunodeficiency virus type-1 (HIV-1) binds to its target RNA, TAR, and activates transcription. A 36-amino acid peptide portion, Tat(37–72), containing RNA-binding domain of Tat. binds specifically to TAR RNA.

The present invention provides the D form of Tat(37–72) and various fragments and analogs by chemical synthesis. The D peptides have an identical covalent structure, however, D and L peptide molecules are the mirror image of one another in three-dimensional space. Surprisingly, it has been found that these D-peptide specifically bind TAR RNA with high affinities and interacts with RNA in the widened major groove, as determined by electrophoretic mobility shift and site-specific photocrosslinking experiments. The D peptides inhibit the binding of the L peptide to TAR RNA in vitro, and thereby inhibit the Tat trans-activation in vivo. Such results demonstrate that the D-peptides of the present invention can recognize specific nucleic acid structures. Since D-peptide ligands are resistant to degradation by naturally occurring enzymes and do not induce a vigorous humoral immune response, they are thus useful to control protein-nucleic acid interactions in vivo.

Figure 1:
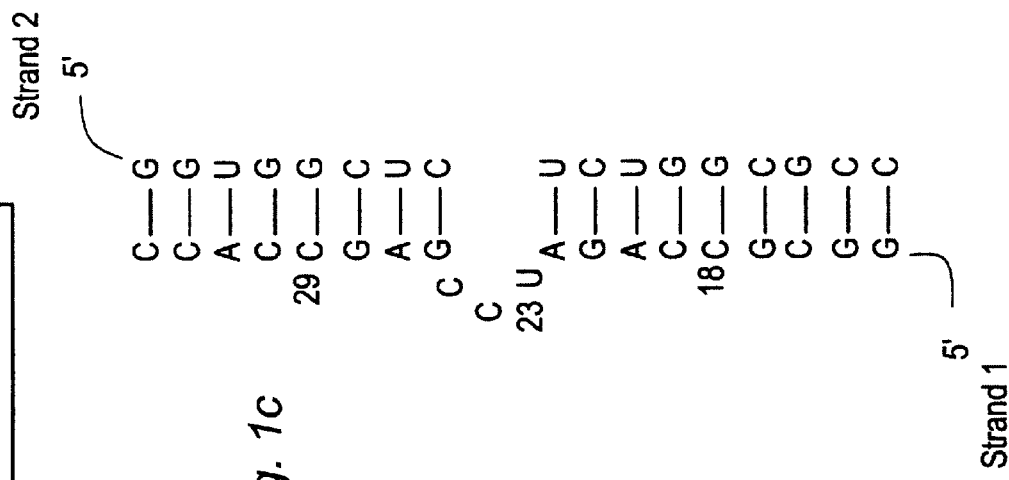
Figure 2:
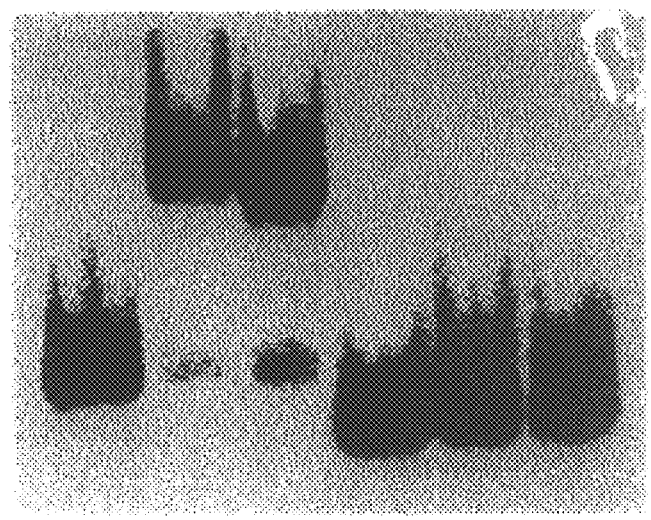

To ascertain whether the D-peptides recognize naturally occurring nucleic acid structures, the D-Tat (37–72) peptide (SEQ ID NO:1, FIG. 1) containing the basic-arginine rich region of Tat was synthesized by solid phase peptide synthesis methods. After HPLC purification and characterization by mass spectrometry, the D-Tat (37–72) peptide (SEQ ID NO:1) was tested for TAR RNA binding (FIG. 2). Similar to L-Tat, the D-Tat (37–72) peptide (SEQ ID NO:1) was able to bind TAR RNA and failed to bind a mutant TAR RNA without the bulge residues.

Figures 3A, 3B:
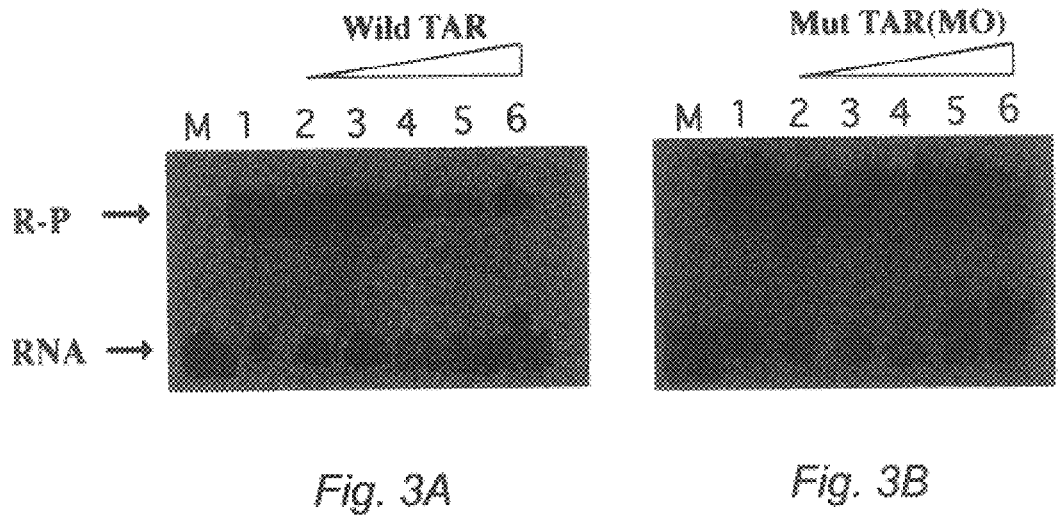

Equilibrium dissociation constants of the D-Tat-TAR RNA complexes were measured by competition electrophoretic mobility assays as shown in FIG. 3. Dissociation constants were calculated from eight sets of experiments which showed that the D-Tat (37–72) peptide (SEQ ID NO:1) binds TAR RNA with a $K_d$ of 0.22 $\mu$M. Under similar experimental conditions, L-Tat(37–72) binds TAR RNA with a $K_d$ of 0.13 $\mu$M. Specificity of the D-Tat-TAR RNA complex formation was addressed by competition experiments (FIG. 3). D-Tat-RNA complex formation was inhibited by the addition of unlabeled wild-type TAR RNA and not by mutant TAR RNA. Mutant TAR RNA without a trinucleotide bulge (FIG. 2 and 3B) or with one base bulge was not able to compete for D-Tat peptide binding to wild-type TAR RNA. Two base-pairs immediately above the pyrimidine bulge are critical for Tat recognition[14].

Figures 3C, 3D:
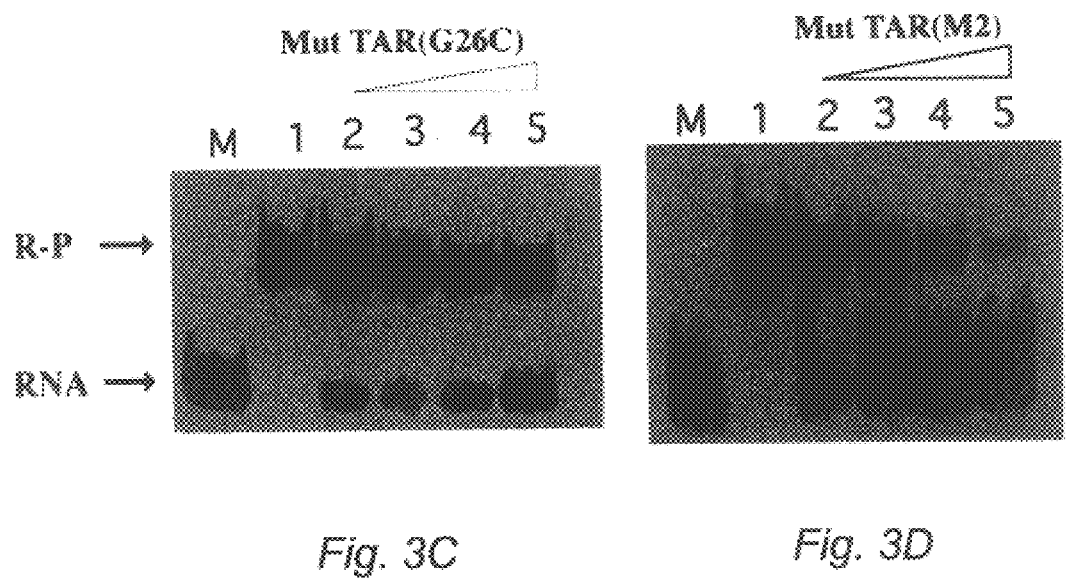

To determine whether D-Tat recognizes specific basepairs in the stem region of TAR RNA or only a trinucleotide bulge containing RNA, a TAR mutant where the G26–C39 base pair was substituted by a C26–G39 base-pair was synthesized. Competition experiments showed that this mutant TAR (G26C) did not inhibit D-Tat binding to TAR RNA (FIG. 3C). These results indicate that the D-Tat peptide can specifically recognize TAR RNA.

While not wishing to be bound by any particular theory, there are a number of ways that the D-Tat peptides could interact with TAR RNA. Several lines of evidence suggest that Tat protein interacts with TAR RNA in a widened major groove[14,21-24]. In a recent study, a rhodium complex, Rh(phen)$_2$phi[3] was used to probe the effect of bulge bases on the major groove width in TAR RNA[23]. These studies establish that there is a correlation between major groove opening and Tat binding. At least a two base bulge is required for major groove widening and other conformational changes to facilitate Tat binding. TAR mutants with a bulge of two uridines, but not one, bind Tat peptides as well as wild-type TAR[12,21]. These data demonstrate that two base bulge containing TAR RNA (M2) can bind the D-Tat peptide and inhibit its binding to wild-type TAR RNA (FIG. 3D); a similar result was obtained with L-Tat peptides.

Figure 4:
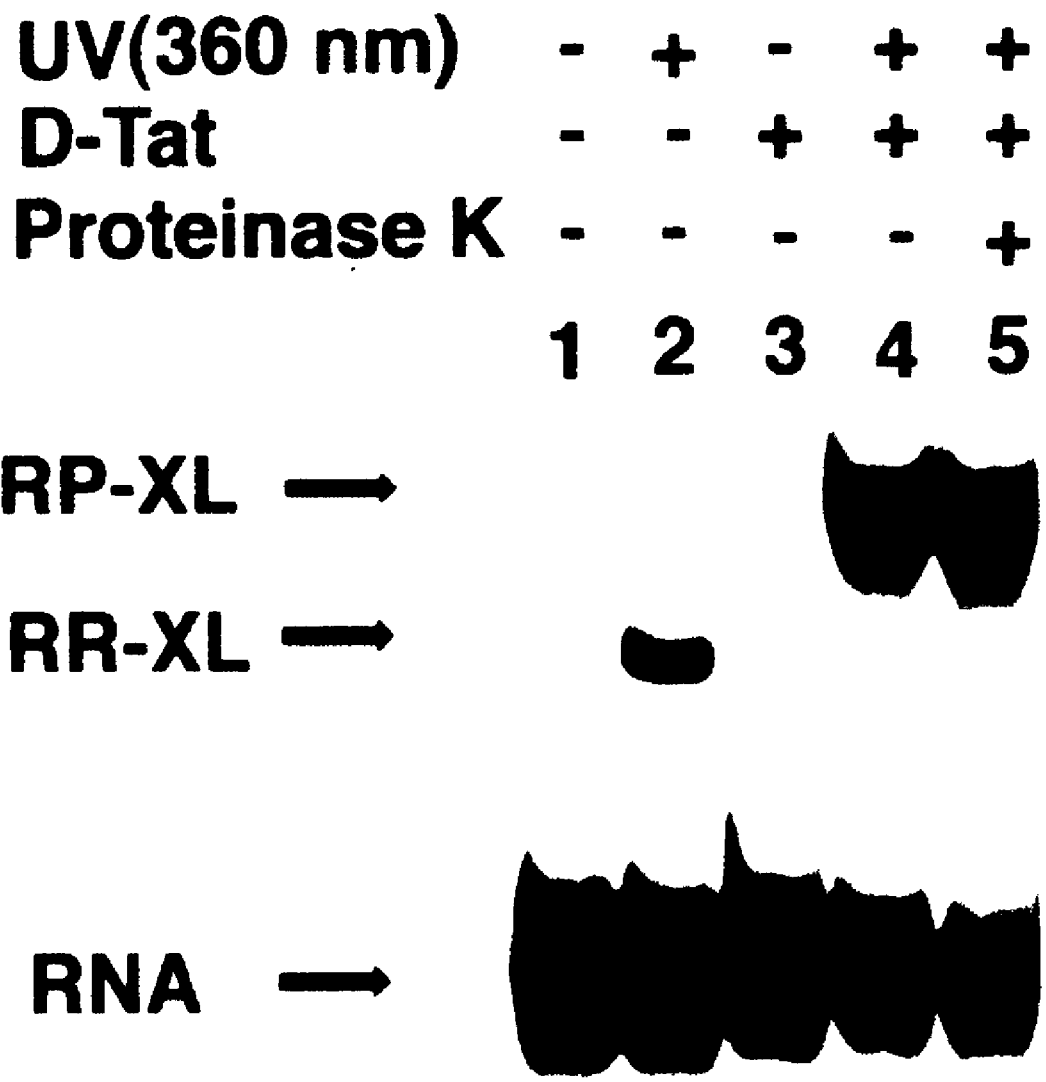

A site-specific crosslinking method based on 4-thio-uracil (4-thioU) photochemistry was used to determine the conformation of TAR RNA and its interaction with Tat protein under physiological conditions. To probe the D-Tat-RNA interactions, TAR RNA containing 4-thioU at position 23 was synthesized and photocrosslinking experiments were performed as shown in FIG. 4. Irradiation of the D-Tat-RNA complex yields a new band with electrophoretic mobility less than that of the RNA (FIG. 4, lane 4). Both D-Tat and UV (360 nm) irradiation are required for the formation of this crosslinked RNA-peptide complex (see lanes 3 and 4). Since the crosslinked D-Tat-RNA complex is stable to alkaline pH (9.5), high temperature (85° C.) and denaturing conditions (8M urea, 2% SDS), it can be concluded that a covalent bond is formed between TAR RNA and the peptide during the crosslinking reaction.

To test the protease stability of the D-Tat-RNA complexes, the D-Tat-RNA crosslink products were subjected to very vigorous proteinase K digestion which showed that the complexes were completely stable and there were no signs of D-Tat peptide degradation (lane 5). Under similar proteinase K treatment, L-Tat-TAR photocrosslink products resulted in a complete loss of RNA-protein crosslinking and a gain in free RNA as observed by band intensities on the gel[24,25].

The specificity of the crosslinking reaction was established by competition experiments. Crosslinking was inhibited by the addition of unlabeled wild-type TAR RNA and not by a mutant TAR RNA lacking the trinucleotide bulge (data not shown). Therefore, it can be concluded that formation of a specific RNA-protein complex between TAR RNA and D-Tat is necessary for photocrosslinking. As the amount of wild-type competitor RNA was increased, a decrease in RNA-protein crosslink was observed (as expected), however, an increase in RNA-RNA crosslink was also observed. These results and the data shown in FIG. 4 (see lanes 2 and 4) indicate that interstrand RNA crosslink is inhibited by the presence of the RNA-binding D-Tat ligand. A similar result was previously obtained in photocrosslinking experiments employing a 34 amino acid L-Tat fragment and 4-thio-U containing TAR RNA[24].

Figure 5:
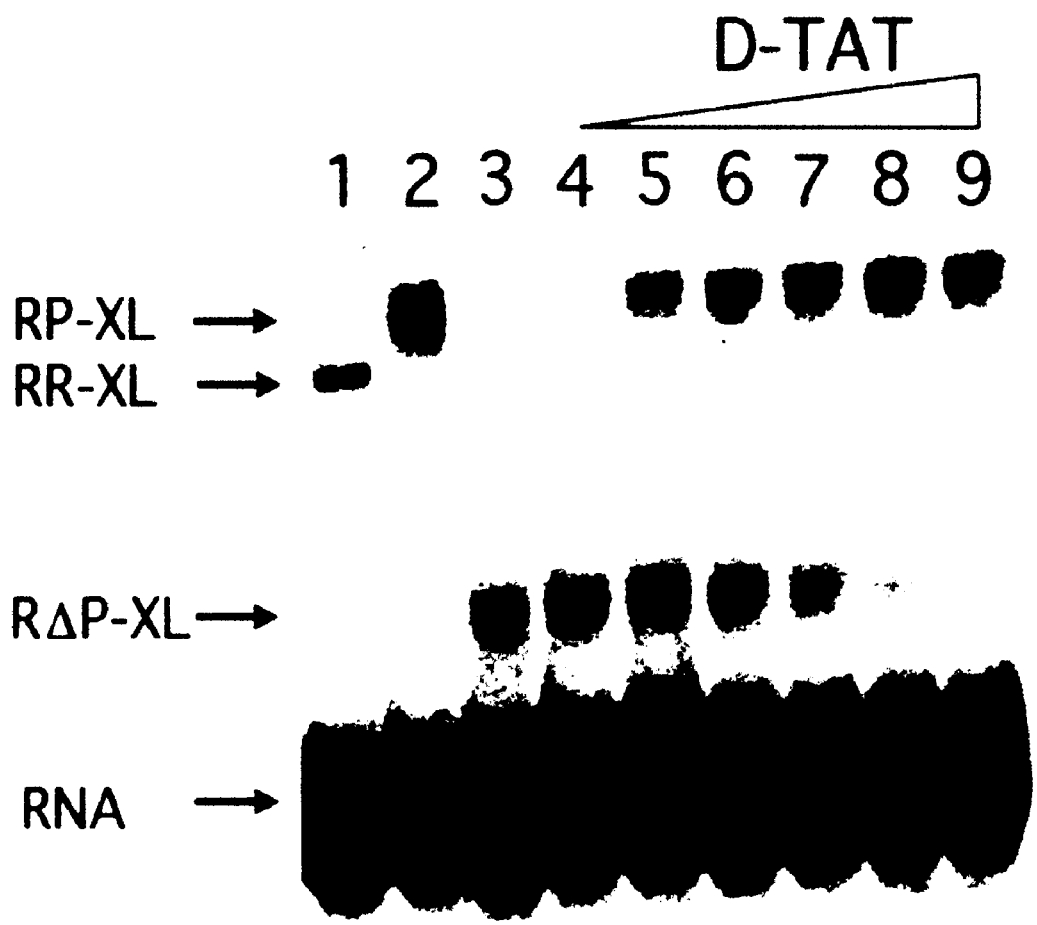

To determine whether D-Tat peptides can inhibit L-Tat-TAR complex formation in vitro, photocrosslinking experiments of the L-Tat-TAR complex were carried out in the presence of increasing amounts of D-Tat followed by proteinase K digestion (FIG. 5). An RNA-protein crosslink was observed in L-Tat-TAR complex (lane 2) which was degraded to smaller RNA-peptide complexes by the addition of proteinase K enzyme (lane 3). Since D-Tat-TAR crosslink is resistant to proteolysis, increasing the amount of D-Tat prior to the crosslinking reactions resulted in an increase in RNA-protein crosslink after proteinase K digestion (lanes 4–9). A decrease in smaller RNA-peptide crosslink products was also observed as the concentration of D-Tat was increased. These results demonstrate that D-Tat can compete with L-Tat to form a complex with TAR RNA in vitro.

To determine if D-Tat peptides inhibits Tat transactivation in vivo, D-Tat with pSV2-Tat[26] and pAL[27] plasmids was crossfected into HeLa cells containing an integrated LTR-CAT reporter[28]. Plasmids pSV2Tat and pAL express first exon of Tat protein and luciferase enzyme, respectively. Transfection of pSV2Tat enhanced transcription as determined by CAT activity. As shown in FIG. 6, increasing amount of the D-Tat (37–72) peptide resulted in a decrease of CAT activity while luciferase activity was not affected. Tat trans-activation was inhibited more than 50% by 5$\mu$g D-Tat peptide. Transfection of L-Tat peptides did not decrease CAT activity suggesting that L-peptides are not stable to proteolysis in vivo. Thus, these results indicate that the D-Tat (37–72) peptide (SEQ ID NO:1) specifically inhibits trans-activation by Tat protein.

These findings indicate that a the Tat-derived D-Tat peptides of the present invention bind TAR RNA specifically and interact in the widened major groove of TAR RNA in a similar fashion to that observed for L-Tat. As shown in a model (FIG. 7), the non-structured region of L and D-Tat peptides displays arginine side chains on the surface for RENA binding. Therefore, symmetry of arginine residues is not critical for RNA recognition as long as arginine side chains can contact accessible functional groups in the major groove of RNA. RNA recognition by D-peptides provides a new approach for the design of cell-permeable and stable molecules for the control of cellular processes involving RNA-protein interactions in vivo.

The utility of the peptides of formula I is further demonstrated by their ability to inhibit replication of HIV-1 in an acute infection assay.

A similar approach has been reported using the cationic peptide, N-acetyl-(DArg)$_9$-NH$_2$ (SEQ ID NO:3). Antiviral activity of that peptide, however, was found to be via inhibition of viral entry, consistent with antiviral activity being observed when the cells were pretreated with peptide 24 hours prior to infection. In that study, the possibility of inhibition of transactivation by blocking Tat protein was suggested, but not proven, and no evidence of the peptide displaying specificity for TAR RNA was presented.

The instant invention thus provides a method of treating a retroviral protease infection in a mammal in need of such treatment. More particularly, the peptides of the present invention can be utilized as Tat protein RNA-binding domain mimics to treat the HIV-1 infection, and the resultant AIDS. The mammal under treatment can be a human, monkey, cat or the like, with the treatment of humans being particularly preferred. A Tat antagonist should also be useful for ameliorating the pathogenic effects of Tat protein on host cells due to interactions with TAR-like elements on cellular transcripts. Recent studies on peptide analogs of the core domain sequence of Tat protein, which is believed to interact with hose cell factors rather than with virally encoded RNA, have lead to the same suggestion for a new class of therapeutic agents for AIDS based on inhibition of the transactivation step in the HIV-1 replication cycle.

The polypeptide of formula I and its fragments and analogs can be synthesized by conventional solution methods, or by solid phase synthetic techniques known in the art.

Throughout the specification and appended claims, the polypeptide of formula I, and its fragments analogs and salts, encompass all stereo, optical and geometrical isomers thereof where such isomers exist, as well as the pharmaceutically acceptable salts and solvates thereof. Where appropriate, the polypeptide or its analogs can be utilized as its corresponding amide form. It is preferred that the amino acid residues described herein are in the "D" isomeric form. However, minor amounts of residues in the "L" isomeric form can be substituted for any D-amino acid residue, as long as the desired functional property is retained by the polypeptide. Preferably, the majority of the amino acids are in the D-form.

The term "biologically and pharmaceutically acceptable salts" is intended to include any such salt derived from an inorganic or organic acid which is tolerated by the mammalian system. These salts include, but are not limited to, acetate, adipate, alginate, citrate, aspartate, benzoate, benzenesulfonate, bisulfate, hexanoate, succinate, fumarate, hydrochloride, hydrobromide, lactate, maleate, phosphate, sulfate, methanesulfonate, oxalate, propionate, tosylate, and mesylate. Examples of acids which can be used to form such salts include such inorganic acids as hydrochloric acid, sulfuric acid and phosphoric acid, and such organic acids such as oxalic acid, maleic acid, succinic acid and citric acid.

The nomenclature used to define the polypeptides is that specified by Schroder & Lubke, "The Peptides", Academic Press (1965), wherein in accordance with conventional representation the amino group at the N-terminal appears to the left and the carboxyl group at the C-terminal to the right. NH$_2$ refers to the free amino group present at the amino terminus of a polypeptide. COOH refers to the free carboxy group present at the carboxy terminus of a polypeptide.

Accordingly, polypeptide analogs displaying substantially equivalent activity to the polypeptide of formula I are likewise contemplated for use in the present invention. These modifications can be obtained through peptide synthesis utilizing the appropriate starting material.

Also, the term "active agent," "active ingredient" and "active medicament" are intended to include within their scope the polypeptide of formula I specifically recited herein as well as all substantially homologous analogs and allelic variations thereof.

In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | AMINO ACID |
| 1-Letter | 3-Letter | |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

An amino acid in the polypeptide of this invention can be changed in a non-conservative manner (i.e., by changing an amino acid belonging to a grouping of amino acids having a particular size or characteristic to an amino acid belonging to another grouping) or in a conservative manner (i.e., by changing an amino acid belonging to a grouping of amino acids having a particular size or characteristic to an amino acid belonging to the same grouping). Such a conservative change generally leads to less change in the structure and function of the resulting polypeptide. The present invention should be considered to include analogs whose sequences contain conservative changes which do not significantly alter the activity or binding characteristics of the resulting polypeptide.

The following is one example of various groupings of amino acids:
Amino Acids with Nonpolar R Groups
  Alanine
  Valine
  Leucine
  Isoleucine
  Proline
  Phenylalanine
  Tryptophan
  Methionine
Amino Acids with Uncharged Polar R Groups
  Glycine
  Serine
  Threonine
  Cysteine
  Tyrosine
  Asparagine
  Glutamine
Amino Acids with Charged Polar R Groups (Negatively Charged at Ph 6.0)
  Aspartic acid
  Glutamic acid
Basic Amino Acids (Positively Charged at pH 6.0)
  Lysine
  Arainine
  Histidine (at pH 6.0)
Another grouping may be those amino acids with phenyl groups:
  Phenylalanine
  Tryptophan
  Tyrosine
Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Gin for Arg or Lys; and
His for Lys or Arg.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the polypeptide's structure.

A preferred group of fragments are tripeptides which contain at least one arginine (Arg) or lysine (Lys) amino acid and at least one of the amino acids is in the D-form. These smaller fragments bind to HIV-1 Tar RNA, and have enhanced cellular uptake due, to their smaller size.

Representative fragments are analogs of the polypeptide of formula I thus include:

1 D-Leu D-Lys Xaa (wherein Xaa is any naturally occurring amino acid sidechain)
2 L-Ser-L-Arg-D-Ala
3 L-Ser-L-Asn-D-Val 4 L-Arg-D-Val-D-Val
5 D-Arg-L-Val-L-Val
6 L-Arg-D-Val-D-Gin
7 D-Lys-L-Lys-L-Val
8 D-Leu-D-Arg-D-Ala
9 L-Arg-D-Val-D-Ala
10 L-Arg-D-Thr-L-Val
11 L-Arg-D-Lys-L-Ala
12 L-Lys-D-Arg-D-Val
13 L-Ala-D-Leu-D-Lys
14 D-Lys-D-Ser-D-Lys
15 L-Ala-D-Arg-L-Asn
16 D-Lys-D-Arg-L-Ala
17 L-Arg-D-Ser-D-Asn
18 D-Ala-D-Lys-D-Lys
19 D-Lys-L-Asn-D-Val
20 D-Lys-L-Gln-D-Val
21 D-Ala-L-Arg-D-Leu
22 L-Arg-D-Val-L-Lys
23 Gly-L-Arg-D-Val
24 L-Arg-D-Leu-D-Phe
25 D-Lys-L-Lys-D-Ala
26 D-Ala-L-Pro-L-Lys
27 D-Lys-D-Asp-L-Lys
28 D-Lys-L-Pro-D-Lys
29 D-Lys-D-Arg-D-Val
30 D-Lys-D-Ara-L-Leu
31 L-Arg-D-Ser-D-Asn
32 D-Arg-D-Ala-D-His

The active peptide compound for use in the present invention can be, and is preferably, administered as a medicament, i.e., a pharmaceutical composition. As discussed earlier, the polypeptides and their analogs of the present invention, may be prepared in pharmaceutical compositions, with a suitable carrier and at a strength effective for administration by various means to a patient experiencing an adverse medical condition associated with specific neuronal degeneration for the treatment thereof. A variety of administrative techniques may be utilized, among them parenteral techniques such as subcutaneous, intravenous and intraperitoneal injections, catheterizations and the like. Average quantities of the polypeptide or its fragments or analogs may vary and in particular should be based upon the recommendations and prescription of a qualified physician.

The pharmaceutical compositions used in the methods of this invention for administration to animals and humans comprise the active compound in combination with a pharmaceutical carrier or excipient.

The medicament can be in the form of tablets (including lozenges and granules), dragees, capsules, pills, ampoules, intranasal sprays, or suppositories comprising the compound of the invention.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of the active compound of the invention in association with a carrier and/or enclosed within an envelope. Whether the medicament contains a daily dose, or, for example, a half, a third or a quarter of a daily dose will depend on whether the medicament is to be administered once, or, for example, twice three times or four times a day, respectively.

Advantageously, the compositions are formulated as dosage units, each unit being adapted to supply a fixed dose of active ingredients. Tablets, coated tablets, capsules, ampoules, intranasal sprays and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician.

The active compound can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch. sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethylene glycols.

The tablets, dragees, capsules and pills comprising the active compound can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The active ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g., cocoa oil and high esters, (e.g., $C_{14}$-alcohol with $C_{16}$-fatty acid)) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol. isopropyl alcohol, ethyl carbonate, ethyl acetate, benzyl alcohol, benzyl benzoate. propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof.

For parenteral and intranasal administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum methahydroxide, bentonite, agar-agar and tragacanth, or mixtures thereof.

The pharmaceutical compositions can also contain coloring agents and preservatives, as well as perfumes and flavoring additions (e.g., peppermint oil and eucalyptus oil, and sweetening agents, (e.g., saccharin and aspartame).

The pharmaceutical compositions will generally contain from 0.5 to 90% of the active ingredient by weight of the total composition.

In addition to the active compound, the pharmaceutical compositions and medicaments can also contain other pharmaceutically active compounds.

Any diluent in the medicaments of the present invention may be any of those mentioned above in relation to the pharmaceutical compositions. Such medicaments may include solvents of molecular weight less than 200 as the sole diluent.

It is envisaged that this active compound will be administered perorally, intranasally, parenterally (for example, intramuscularly, intrathecally, intraperitoneally, subcutaneously, transdermally or intravenously), rectally or locally, preferably intranasally or parenterally, especially perlingually, or intravenously. Most preferably, the peptide of formula I, or its analog or salt, is administered by the intranasal or intravenous route.

The dosage rate, is preferably in the range of 0.01 to 20 mg/kg of body weight, and most preferably in the range of 0.5 to 5 mg/kg of body weight, and will be a function of the nature and body weight of the subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day. In this regard, the intranasal administration mav utilize metered dose devices known in the art.

The following examples are presented in order to more fully illustrate the preferred embodiments of the invention. They should in no way be construed, however, as limiting the broad scope of the invention. The following examples are presented in order to more fully illustrate the preferred embodiments of the invention. They should in no way be construed, however, as limiting the broad scope of the invention.

EXAMPLES

Example 1

Methods
RNA and Tat-derived Peptide Synthesis

All RNAs were prepared by in vitro transcription[29]. For transcription reactions (20 μL) containing 8.0 pmoles template DNA, 40–60 units of T7 polymerase (Promega) was used. For the synthesis of 4-thioU labeled RNA, UTP was replaced with 4-thioUTP (4 mM, final concentration) in the transcription buffer. 4-thio-UTP was synthesized according to the method of[30]. RNA purification and labeling were carried out as described in Wang et al., $Biochemistry$ 35, 6491–6499 (1996).

Tat-derived peptides, fragments and analogs were synthesized on an ABI 431 peptide synthesizer by using N-α-Fmoc-protected monomers[24]. After cleavage from the resin, the peptides were purified by HPLC on a Zorbax 300 SB-$C_8$ column. The mass of fully deprotected and purified peptide was confirmed by FAB mass spectrometry; 4186.8 (M+H).

Gel-Shift Assays $^{32}$P-5'-end labeled TAR RNAs were heated to 85° C. for 3 minutes and then cooled to room temperature in TK buffer (50 mM Tris-HCl (pH 7.4), 20 mM KCl, 0.1% Triton X-100). The Tat peptide was added alone or along with the competitor RNAs (wild-type TAR or mutant TAR) preheated in TK buffer at 85° C. for 3 minutes and cooled to room temperature. The peptide-RNA binding reactions were carried out at room temperature for 1 hour and stopped by adding 30% glycerol. The peptide-RNA complexes were resolved on a non-denaturing 12% acrylamide gel and visualized by autoradiography or Phosphorimaging.

Site-Specific Photo-Cross-Linking Reactions

For photochemical reactions, RNA duplex was prepared by hybridizing two strands [24]. Strand 1 of the duplex was 5'-end labeled with $^{32}$P. Preformed RNA duplexes(0.02 μM) in the absence or presence of the peptide (0.1 μM) were irradiated (360 mn) and analyzed by denaturing gels as described in Wang et al., $Biochemistry$ 35, 6491–6499 (1996).

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The documents should be considered as incorporated by reference in their entirety.

1. Jones, K. A. & Peterlin, B. M. $Annu. Rev. Biochem.$ 63:71743 (1994).
2. Jeang, K.-T., Berkhout, B. & Dropulic, B. $J. Biol. Chem.$ 268:24940–24949 (1993).
3. Gaynor, R. $AIDS$ 6:347–63 (1992).
4. Fisher, A.G., et al. $Nature$ 320:367–371 (1986).
5. Dayton, A. I., Sodroski, J. G., Rosen, C. A., Goh, W. C. & Haseltine, W. A. $Cell$ 44:941–947 (1986).
6. Cullen, B. R. $Microbiol. Rev.$ 56:375–394 (1992).
7. Cordingley, M. G., et al. $Proc. Natl. Acad. Sci.$ 87:8985–8989 (1990).
8. Weeks, K. M., Ampe, C., Schultz, S. C., Steitz, T. A. & Crothers, D. M. $Science$ 249:1281–1285 (1990).
9. Calnan, B. J., Biancalana, S., Hudson, D. & Frankel, A. D. $Genes Dev.$ 5:201–210 (1991).
10. Calnan, B. J., Tidor, B., Biancalana, S., Hudson, D. & Frankel, A. D. $Science$ 252:1167–1171 (1991).
11. Delling, U., et al. $Proc. Narl. Acad. Sci.$ 88:6234–6238 (1991).
12. Sumner-Smith, M., et al. $J. Virol.$ 65:5196–5202 (1991).
13. Weeks, K. M. & Crothers, D. M. $Science$ 261:1574–1577 (1993).
14. Churcher, M. J., et al. $J. Mol. Biol.$ 230:90–110 (i993).
15. Bayer, P., et.al. $J. Mol. Biol.$ 247:529–535 (1995).
16. Milton, R. C., Milton, S. C. & Kent, S. B. $Science$ 256:1445–8 (1992).
17. Zawadzke, L. E. & Berg, J. M. $J. Am. Chem. Soc.$ 114:4002 (1992).
18. Zawadzke, L. E. & Berg, J. M. $Proteins$ 16:301–5 (1993).
19. Schumacher, T. N. M., et al. $Science$ 271:1854–1857 (1996).

20. Dintzis, H. M., Symer, D. E., Dintzis, R. Z., Zawadzke, L. E. & Berg, J. M. *Proteins* 16:306–8 (1993).
21. Weeks, K. M. & Crothers, D. M. *Cell* 66:577–588 (1991).
22. Hamy, F., etal. *J. Mol. Biol.* 230:111–123 (1993).
23. Neenhold, H. R. & Rana, T. M. *Biochremistry* 34:6303–6309 (1995).
24. Wang, Z. & Rana, T. M. *Biochemistry* 35:6491–6499 (1996).
25. Wang, Z., Wang, X. & Rana, T. M. *J. Biol. Chem.* 271:16995–16998 (1996).
26. Frankel, A. D. & Pabo, C. O. *Cell* 55:1189–1194 (1988).
27. Nordeen, S. K. *Biotechniques* 6:454457 (1988).
28. Felber, B. K. & Paviakis, G. N. *Science* 239:184–187 (1988).
29. Milligan, J. F., Groebe, D. R., Witherell, G. W. & Uhlenbeck, O. C. *Nucl. Acids Res.* 15:8783–8798 (1987).
30. Stade, K., Rinke-Appel, J. & Brimacombe, R. *Nucl. Acids Res.* 17:9889–9909 (1989).
31. Jakobovits, A., Smith, D. H., Jakobovits, E. B. & Capon, D. J. *Mol. Cell. Biol.* 8:2555–2561 (1988).
32. Aboul-ela, F., Karn, J. & Varani, G. *J. Mol. Biol.* 253:313–332 (1995).

What is claimed is:

1. A peptide of the formula
ID-Cys-D-Phe-D-Thr-D-Thr-D-Lys-D-Ala-D-Leu-D-Gly-D-Ile-D-Ser-D-Tyr-D-Gly-D-Arg-D-Lys-D-Lys-D-Arg-D-Arg-D-Gln-D-Arg-D-Arg-D-Arg-D-Pro-D-Pro-D-Gln-D-Gly-D-Ser-D-Gln-D-Thr-D-His-D-Gln-D-Val-D-Ser-D-Leu-D-Ser-D-Lys-D-Gln (SEQ ID NO: 1) and the biologically and pharmaceutically acceptable salts thereof.

2. The peptide of claim 1 wherein the C-terminal residue contains an amide group.

3. A pharmaceutical composition comprising a peptide of the formula
D-Cys-D-Phe-D-Thr-D-Thr-D-Lys-D-Ala-D-Leu-D-Gly-D-Ile-D-Ser-D-Tyr-D-Gly-D-Arg-D-Lys-D-Lys-D-Arg-D-Arg-D-Gln-D-Arg-D-Arg-D-Arg-D-Pro-D-Pro-D-Gln-D-Gly-D-Ser-D-Gln-D-Thr-D-His-D-Gln-D-Val-D-Ser-D-Leu-D-Ser-D-Lys-D-Gln (SEQ ID NO: 1) or a biologically and pharmaceutically acceptable salt thereof, and a pharmaceutically acceptable carrier therefor.

4. The composition of claim 3 wherein the C-terminal residue of the peptide contains an amide group.

5. The composition of claim 3 adapted for parenteral administration.

* * * * *